(12) United States Patent  (10) Patent No.: US 8,343,332 B2
Brown  (45) Date of Patent: *Jan. 1, 2013

(54) ELECTROCHEMICAL TEST SENSOR

(75) Inventor: Daniel V. Brown, Chappaqua, NY (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/161,953

(22) Filed: Jun. 16, 2011

(65) Prior Publication Data

US 2011/0247944 A1 Oct. 13, 2011

Related U.S. Application Data

(63) Continuation of application No. 11/825,231, filed on Jul. 5, 2007, now Pat. No. 7,993,512.

(60) Provisional application No. 60/819,961, filed on Jul. 11, 2006.

(51) Int. Cl.
*G01N 27/327* (2006.01)
(52) U.S. Cl. .................. 205/777.5; 204/403.14
(58) Field of Classification Search ........... 205/777.5, 205/792; 204/403.01, 403.02, 403.04, 403.14
See application file for complete search history.

(56) References Cited

U.S. PATENT DOCUMENTS

| 4,935,346 A | 6/1990 | Phillips et al. ............... 435/14 |
| 5,049,394 A | 9/1991 | Howard et al. .............. 424/490 |
| 5,049,487 A | 9/1991 | Phillips et al. ............... 435/4 |
| 5,120,420 A | 6/1992 | Nankai et al. ................ 204/403 |
| 5,128,015 A | 7/1992 | Szuminsky et al. ........... 204/403 |
| 5,179,005 A | 1/1993 | Phillips et al. ............... 435/14 |
| 5,304,468 A | 4/1994 | Phillips et al. ............... 435/14 |
| 5,512,159 A | 4/1996 | Yoshioka et al. ............. 204/403 |
| 5,552,027 A | 9/1996 | Birkle et al. ................. 204/290 F |
| 5,582,697 A | 12/1996 | Ikeda et al. .................. 204/403 |
| 5,628,890 A | 5/1997 | Carter et al. ................. 204/403 |
| 5,660,791 A | 8/1997 | Brenneman et al. .......... 422/58 |
| 5,723,345 A | 3/1998 | Yamauchi et al. ............ 436/518 |

(Continued)

FOREIGN PATENT DOCUMENTS

EP 0 735 363 A1 10/1996

(Continued)

OTHER PUBLICATIONS

International Search Report corresponding to International Patent Application No. PCT/US2007/015640, European Patent Office, dated Jan. 22, 2008, 3 pages.

(Continued)

*Primary Examiner* — J. Christopher Ball
(74) *Attorney, Agent, or Firm* — Nixon Peabody LLP (57) ABSTRACT

An electrochemical test sensor for detecting the concentration of an analyte in a sample. The electrochemical test sensor comprises a base that provides a flow path for the fluid test sample having a counter electrode and a working electrode on its surface in electrical communication with a detector of electrical current. The electrochemical test sensor further includes a reagent layer directly located on the surface of the working electrode. The reagent layer includes an enzyme that is adapted to react with the analyte. The electrochemical test sensor further comprises a lid adapted to mate with the base and to assist in forming a capillary space with an opening for the introduction of the sample thereto. The capillary space is formed with a three-dimensional portion of the lid.

18 Claims, 5 Drawing Sheets

U.S. PATENT DOCUMENTS

| | | | |
|---|---|---|---|
| 5,759,364 A | 6/1998 | Charlton et al. | 204/403 |
| 5,789,255 A | 8/1998 | Yu | 536/95 |
| 5,798,031 A | 8/1998 | Charlton et al. | 204/403 |
| 6,076,645 A | 6/2000 | Winkelmann et al. | 192/85 CA |
| 6,193,865 B1 | 2/2001 | Hodges et al. | 204/435 |
| 6,484,046 B1 | 11/2002 | Say et al. | 600/345 |
| 6,485,923 B1 | 11/2002 | Yani et al. | 435/14 |
| 6,531,040 B2 | 3/2003 | Musho et al. | 204/401 |
| 6,576,102 B1 | 6/2003 | Rappin et al. | 204/403 |
| 6,841,052 B2 | 1/2005 | Musho et al. | 204/401 |
| 6,960,287 B2 | 11/2005 | Charlton | 205/775 |
| 7,118,668 B1 | 10/2006 | Edelbrock et al. | 205/777.5 |
| 7,122,102 B2 | 10/2006 | Wogoman | 204/400 |
| 7,122,110 B2 | 10/2006 | Deng et al. | 205/777.5 |
| 7,125,481 B2 | 10/2006 | Musho et al. | 205/775 |
| 7,132,041 B2 | 11/2006 | Deng et al. | 205/777.5 |
| 7,294,246 B2 | 11/2007 | Gundel et al. | 204/403.14 |
| 2001/0042683 A1 | 11/2001 | Musho et al. | 204/403 |
| 2002/0175075 A1 | 11/2002 | Deng et al. | 204/403.01 |
| 2003/0094367 A1 | 5/2003 | Bhullar et al. | 204/403.1 |
| 2004/0007461 A1 | 1/2004 | Edelbrock et al. | 204/403.11 |
| 2005/0098434 A1* | 5/2005 | Gundel et al. | 204/403.02 |
| 2005/0100880 A1 | 5/2005 | Chang | 435/4 |
| 2007/0045127 A1 | 3/2007 | Huang et al. | 205/777.5 |

FOREIGN PATENT DOCUMENTS

| | | |
|---|---|---|
| EP | 1 074 832 A1 | 2/2001 |
| EP | 1 130 390 A1 | 9/2001 |
| EP | 1 275 732 A1 | 1/2003 |
| EP | 0 732 406 B1 | 10/2004 |
| JP | H10-318970 | 12/1998 |
| JP | 2002-195972 | 7/2002 |
| JP | 2003-028828 | 1/2003 |
| WO | WO 99/13099 | 3/1999 |
| WO | WO 2005/078437 A1 | 8/2005 |

OTHER PUBLICATIONS

Written Opinion corresponding to International Patent Application No. PCT/US2007/015640, European Patent Office, dated Jan. 22, 2008, 6 pages.

* cited by examiner

ELECTROCHEMICAL TEST SENSOR

CROSS REFERENCE TO RELATED APPLICATION

This application is a continuation of pending U.S. patent application Ser. No. 11/825,231, filed Jul. 5, 2007, titled "Electrochemical Test Sensor," which claims the benefit of priority from U.S. Provisional Application No. 60/819,961, filed Jul. 11, 2006, which are hereby incorporated by reference in their entirety.

FIELD OF THE INVENTION

The present invention relates generally to electrochemical test sensors, and more specifically to a test sensor that is adapted to determine the concentration of an analyte.

BACKGROUND OF THE INVENTION

Medical conditions such as diabetes require a person afflicted with the condition to regularly self-monitor that person's blood-glucose concentration level. The purpose of monitoring the blood glucose concentration level is to determine the person's blood glucose concentration level and then to take corrective action, based upon whether the level is too high or too low, to bring the level back within a normal range. The failure to take corrective action may have serious medical implications for that person.

One method of monitoring a person's blood glucose level is with a portable testing device. The portable nature of these devices enables users to conveniently test their blood glucose levels at different locations. One type of device utilizes an electrochemical test sensor to harvest the blood sample and to analyze the blood sample. Some electrochemical test sensors include a substrate with electrodes, a dielectric layer, and reagent layers that are screen-printed in succession. A capillary channel for receiving the fluid sample may be formed by affixing a three-dimensional embossed lid, or a spacer and lid on top of it. The dielectric layer in these test sensors defines the area of the electrodes and reagent to be contacted by the blood sample. A defined area is important because the measured current is dependent both on the analyte concentration and the area of the working electrode, which is exposed to the analyte-containing test sample and the reagent layer.

Mass production of electrochemical test sensors is not an inexpensive process. The cost of the process can be decreased by, for example, reducing the number of components or increasing the efficiency of the process itself. Thus, there exists a need for a test sensor that is less costly to produce while still maintaining an accurate measurement of the analyte.

Furthermore, some electrochemical test sensor devices have larger capillary channels than are optimally desirable. The bigger the capillary channel, the more blood from a person is required to fill the channel. Because drawing blood from a person is unpleasant, it would also be desirable to reduce the size of the capillary channel to require less blood, which should reduce the time for taking and testing such a sample. Thus, there also exists a need for a test sensor with a smaller capillary channel.

SUMMARY OF THE INVENTION

An electrochemical test sensor for detecting the concentration of analyte in a fluid test sample is disclosed according to one embodiment of the present invention. The electrochemical test sensor comprises a base that provides a flow path for the fluid test sample having a counter electrode and a working electrode on its surface in electrical communication with a detector of electrical current. The electrochemical test sensor further includes a reagent layer directly located on the surface of the working electrode. The reagent layer includes an enzyme that is adapted to react with the analyte. The electrochemical test sensor also comprises a lid adapted to mate with the base and to assist in forming a capillary space with an opening for the introduction of fluid test sample thereto. The capillary space is formed with a three-dimensional portion of the lid.

An electrochemical test sensor for detecting the concentration of analyte in a fluid test sample according to another embodiment of the present invention is disclosed. The electrochemical test sensor comprises a base that provides a flow path for the fluid test sample having on its surface a counter electrode and a working electrode in electrical communication with a detector of electrical current. A reagent layer is directly located on the surface of the working electrode and includes an enzyme that is adapted to react with the analyte. The working electrode includes a main portion having a first width in a first direction and further includes at least one secondary portion extending from the main portion having a second width in the first direction. The first width is at least about 2 times greater than the second width. The electrochemical test sensor further comprises a lid adapted to mate with the base and to assist in forming a capillary space with an opening for the introduction of fluid test sample thereto.

An electrochemical test sensor for detecting the concentration of analyte in a fluid test sample is disclosed according to yet an alternative embodiment of the present invention. The electrochemical test sensor comprises a base that provides a flow path for the fluid test sample having on its surface a counter electrode and a working electrode in electrical communication with a detector of electrical current. The working electrode includes a main portion and at least two secondary portions extending therefrom. A reagent layer is directly located on the surface of the working electrode and includes an enzyme that is adapted to react with the analyte. The electrochemical test sensor further includes a lid that is adapted to mate with the base and to assist in forming a capillary space with an opening for the introduction of fluid test sample thereto.

A method for determining the concentration of an analyte in a fluid test sample with a test sensor is disclosed according to one process of the present invention. The method comprises the act of providing a base that provides a flow path for the fluid test sample having on its surface a counter electrode and a working electrode in electrical communication with a detector of electrical current. The working electrode includes a main portion and at least two secondary portions extending therefrom. A reagent layer is directly located on the surface of the working electrode. The reagent layer includes an enzyme that is adapted to react with the analyte. A lid is adapted to mate with the base and to assist in forming a capillary space with an opening for the introduction of fluid test sample thereto. The method further comprises the act of contacting the reagent layer with the fluid sample via the capillary space. The method additionally includes the act of generating an electrical signal in the test sensor in response to the presence of the analyte. Still further, the method comprises the act of determining the concentration of the analyte from the electrical signal.

A method for determining the concentration of an analyte in a fluid sample with a test sensor is disclosed according to one process of the present invention. The method comprises the act of providing an electrochemical test sensor comprising a base that provides a flow path for the fluid test sample having on its surface a counter electrode and a working electrode in electrical communication with a detector of electrical current. A reagent layer is directly located on the surface of the working electrode. The reagent layer includes an enzyme that is adapted to react with the analyte. A lid is adapted to mate with the base and to assist in forming a capillary space with an opening for the introduction of fluid test sample thereto. The capillary space is formed with a three-dimensional portion of the lid. The method further includes the act of contacting the reagent layer with the fluid sample via the capillary space. The method further comprises the act of generating an electrical signal in the test sensor in response to the presence of the analyte. The method further includes the act of determining a level of the analyte from the electrical signal.

The above summary of the present invention is not intended to represent each embodiment, or every aspect, of the present invention. Additional features and benefits of the present invention are apparent from the detailed description and figures set forth below.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents and alternatives falling within the spirit and scope of the invention.

DESCRIPTION OF ILLUSTRATED EMBODIMENTS

The present invention is directed to an electrochemical test sensor that is adapted to be placed into a meter or an instrument and assist in determining an analyte concentration in a body fluid sample. The body fluid sample may be collected with a lancing device. Examples of the types of analytes that may be collected include glucose, lipid profiles (e.g., cholesterol, triglycerides, LDL and HDL), microalbumin, hemoglobin $A_{1C}$, fructose, lactate, or bilirubin. It is contemplated that other analyte concentrations may also be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, analyte level, activity (e.g., enzymes and electrolytes), titers (e.g., antibodies), or any other measure concentration used to measure the desired analyte.

Figure 1:
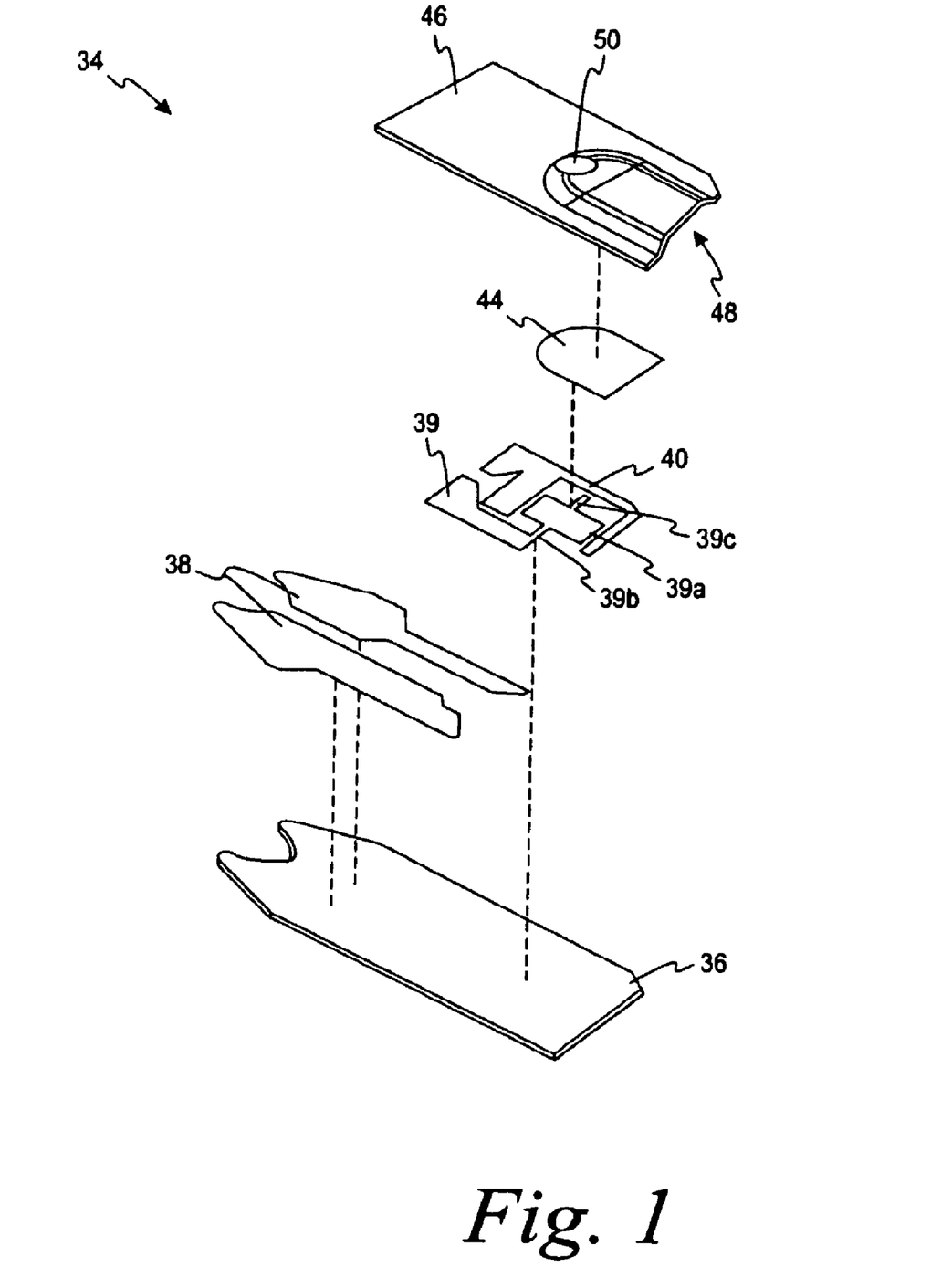
FIG. 1 is an exploded view of an electrochemical test sensor according to one embodiment.

Referring initially to FIG. 1, an electrochemical test sensor 34 includes an insulating base 36, a meter-contact area 38, an electrode pattern (working electrode 39 and counter electrode 40), a reagent layer 44, and a lid 46. The electrochemical test sensor 34 may be printed in sequence such as by screen-printing techniques. It is contemplated that the electrochemical test sensor 34 may be formed by other methods.

The function of the reagent layer 44 is to convert an analyte (e.g., glucose) in the fluid test sample, stoichiometrically into a chemical species that is electrochemically measurable, in terms of electrical current it produces, by the components of the working electrode 39 and counter electrode 40. The reagent layer 44 typically includes an enzyme and an electron acceptor. The enzyme reacts with the analyte to produce mobile electrons on the working and counter electrodes 39, 40. For example, the reagent layer 44 may include glucose oxidase or glucose dehydrogenase if the analyte to be determined is glucose. The enzyme in the reagent layer 44 may be combined with a hydrophilic polymer such as poly(ethylene oxide) or other polymers such as polyethylene oxide (PEO), hydroxyethyl cellulose (HEC), carboxymethylcellulose (CMC) and polyvinyl acetate (PVA). The electron acceptor (e.g., ferricyanide salt) carries the mobile electrons to the surface of the working electrode 39.

The working electrode 39 and the counter electrode 40 assist in electrochemically determining the analyte concentration. In one embodiment, the working electrode 39 and the counter electrode 40 comprise a mixture of amorphous and graphite forms of carbon that is chosen to be electrochemically active and provide a low electrical resistance path between the electrodes and the meter-contact area 38. In another embodiment, the working electrode 39 and the counter electrode 40 comprises a mixture of carbon and silver. It is contemplated that the working electrode 39 and the counter electrode 40 may be made of other materials that assist in providing an electrical path to the meter or instrument with which they are in operative connection. The reagent layer 44, as shown in FIG. 1, is directly located on the electrodes 39 and 40. More specifically, there is not an intervening layer (such as a dielectric layer) between the reagent layer and the electrodes 39 and 40.

A three-dimensional lid 46 forms a concave space 48 over the base 36 and the components located thereon eventually form a capillary space or channel. The lid 46 may be formed by embossing a flat sheet of deformable material and then joining the lid 46 to the base 36 in a sealing operation. The material forming the lid 46 may be a deformable polymeric sheet material (e.g. polycarbonate or an embossable grade of polyethylene terphthalate), or a glycol modified polyethylene terephthatalte. It is contemplated that other materials may be used in forming the lid 46.

The material forming the lid 46 may be punctured to provide at least one air vent 50. The air vent 50 is desirable because it assists in preventing or inhibiting air-lock. By preventing or inhibiting air-lock, a fluid sample is better able to enter the capillary channel 48 in a timely manner.

Suitable materials for the insulating base 36 of FIG. 1 include polymeric materials, such as polycarbonate, polyethylene terephthalate, dimensionally stable vinyl and acrylic polymers, and blends thereof. The insulating base 36 may be formed from metal foil structures such as a nylon/aluminum/polyvinyl chloride laminate. It is contemplated that other materials may be used in forming the insulating base.

The lid 46 and the base 36 may be sealed together by a variety of methods. For example, the lid 46 and the base 36 may be sealed together by sonic welding in which the base 36 and the lid 46 are first aligned and then pressed together between a vibratory heat sealing member or horn and a stationary jaw. In this method, the horn is shaped such that contact is made only with the flat, non-embossed regions of the lid 46. Ultrasonic energy from a crystal or other transducer is used to excite vibrations in the metal horn. This mechanical energy is dissipated as heat in the polymeric joint allowing the bonding of the thermoplastic materials. In another method, the lid 46 and the base 36 are joined by using an adhesive material on the underside of the lid 46. It is contemplated that other methods may be used to attach the lid and the base.

In electrochemical test sensors, it is desirable to have a defined area on the electrode pattern to ensure an accurate meter reading. A defined area is important because the measured current is dependent both on the concentration of the analyte and the area of the working electrode that is exposed to the analyte containing the test sample.

When manufacturing the test sensor 34, the concave space 48 formed by the lid 46 may vary in location over the base 36. This is caused by manufacturing tolerances in forming the lid 46, the base 36, the concave space 48, and the placement of the lid 46 to the base 36. Thus, different areas of the working electrode 39 may be exposed to the fluid test sample via the concave space 48, which may affect the accuracy of the meter reading. Furthermore, if the lid 46 and the base 36 are joined with an adhesive on the underside of the lid 46, there may be some adhesive material "squeeze-out" such that the adhesive material extends past the flat, non-embossed regions of the lid 46 and onto a portion of the working electrode 39 that is exposed to the analyte. The adhesive material "squeeze-out" may affect the reading of the electrochemical test sensor 34. However, the effect of these manufacturing processes is minimized in the present invention due to the shape of, for example, the working electrode 39. In this example, the working electrode may produce consistent readings without using a dielectric layer.

Figure 2:
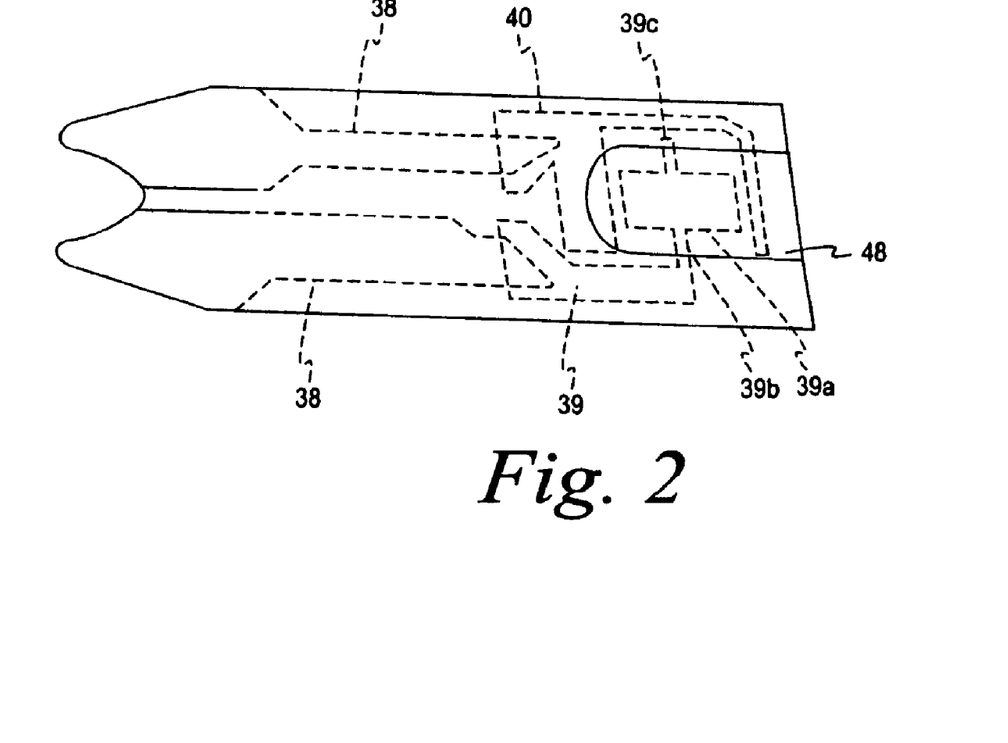
FIG. 2 is a top view of an assembled electrochemical test sensor of FIG. 1.

Referring to FIGS. 1-4, the working electrode 39 includes a main portion 39a and two secondary portions 39b,c. The base 36 includes the electrical conductor pattern 38 on its surface which is in turn overcoated with the working electrode 39 and the counter electrode 40. As best shown in FIG. 2, the portions of the working electrode 39 and the counter electrode 40 are exposed to the fluid test sample in the concave space 48 (i.e., capillary channel).

Figure 3:
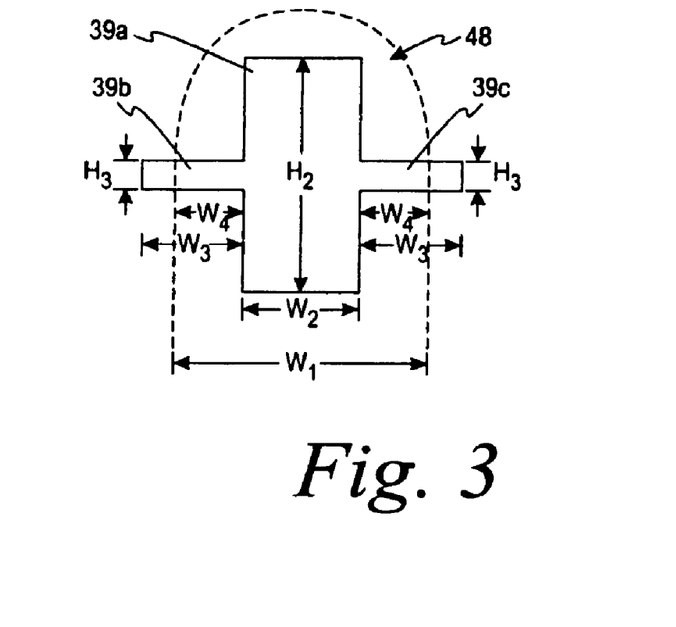
FIG. 3 is an enlarged portion of a working electrode of the electrochemical test sensor generally adapted to contact the test fluid sample and a concave space formed by a lid of the sensor of FIG. 1.

Referring specifically now to FIG. 3, the portion of the working electrode 39 generally adapted to contact the test fluid sample is illustrated with an area being exposed to the fluid test sample via the concave space 48. The working electrode 39 is designed so that the main portion 39a remains fully exposed in the concave space 48 despite the manufacturing variations in locating the concave space 48 with respect to the main portion 39a. As illustrated in FIG. 3, portions of the secondary portions 39b,c of the working electrode 39 are also exposed to the concave space 48. The difference in the area of the main portion 39a in relation to the secondary portions 39b,c assists in obtaining a more accurate analyte concentration reading despite the manufacturing variances because the area of the main portion 39a is substantially larger than the area of the secondary portions 39b,c exposed to the fluid test sample.

Figure 4:
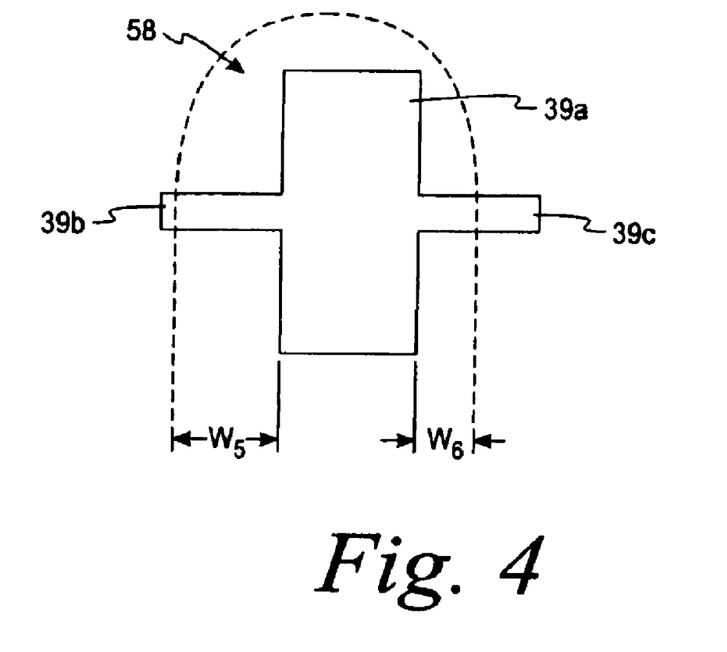
FIG. 4 is an enlarged portion of the working electrode of an electrochemical test sensor generally adapted to contact the test fluid sample and a different concave space formed by a lid of another sensor.

Although the entire main portion 39a of the working electrode 39 desirably remains in the concave space 48 despite the potential for the concave space 48 to vary in location, the area exposed to contact by the fluid test sample of the secondary portions 39b,c may vary due to the mating of the lid 46 and the base 36 (see, for example, the concave space 48 of FIG. 3 compared to a concave space 58 of FIG. 4). However, since the area of the secondary portions 39b,c is a small fraction of the area of the main portion 39a, the variation in contact area of the secondary portions 39b,c does not significantly affect the meter reading. Furthermore, the effect of the adhesive "squeeze-out" onto the secondary portions 39b,c, which may result from the joining of the lid 46 to the base 36, is also minimized due to the small area of the secondary portions 39b,c when compared to the main portion 39a of the working electrode 39.

In FIG. 3, the concave space 48 has a width of about 0.043 inches (identified by arrow $w_1$). The main portion 39a of the working electrode 39 has a width of about 0.023 inches (identified by arrow $w_2$) and a height of about 0.05 inches (identified by arrow $h_2$). The secondary portions 39b,c of the working electrode 39 have a width of about 0.025 inches (identified by arrow $w_3$) and a height of about 0.005 inches (identified by arrow $h_3$). The width of the secondary portions 39b,c (identified by arrow $w_3$) may vary so long as at least some portion of the secondary portions 39b,c extend across the entirety of the capillary width $w_1$. Accordingly, the proportion of the width of the main portion 39a is generally from about 1 to about 5 times the width of the secondary portions 39b,c. The proportion of the width of the main portion 39a is typically greater than about 2 times the width of the secondary portions 39b,c. Furthermore, as can be seen above, the height $h_2$ of the main portion 39a is about 10 times the height $h_3$ of the secondary portions 39b,c. However, the height $h_2$ of the main portion 39a may be about 5 to 15 times the height $h_3$ of the secondary portions 39b,c. As will be discussed further below, the shapes as well as the widths and heights of the main portion may vary.

The area of the main portion 39a of the working electrode is 0.00115 in$^2$, which is the product of its width $w_2$ (0.023 inches) multiplied by its height $h_2$ (0.05 inches). In the illustrated embodiment, the main portion 39a of the working electrode 39 is directly in the center of the width $w_1$ of the concave opening 48. Since the width $w_1$ is 0.043 inches and the main portion 39a is 0.023 inches in width $w_2$, the portion of each secondary portion 39b,c exposed by the concave space 48 is about 0.01 inches [0.043-0.023)/2] (identified by arrow $w_4$). Thus, the area of each secondary portion 39b,c exposed by the concave space 48 is the product of its width $w_4$ (0.01 inches) multiplied by its height $h_3$ (0.005 inches), resulting in a contact area of 0.00005 in$^2$ for each secondary portion 39b,c. The area of the main portion 39a (0.00115 in$^2$) is about 12 times larger than the total area of the secondary portions 39b,c (0.0001 in$^2$) exposed to the fluid test sample. However, other proportions in area may also work in accordance with the present invention. In some embodiments, the total area of the main portion 39a of the working electrode 39 may be about 5 times the size of the area of the secondary portions 39b,c of the working electrode 39. Preferably, the main portion 39a of the working electrode 39 is at least 10 or at least 20 times the size of the area of the secondary portions 39b,c of the working electrode 39.

Referring now to FIG. 4, the concave space 58 is illustrated, which leaves a different area of the working electrode 39 exposed to the fluid test sample than the concave space 48 due to a manufacturing process variance. As mentioned above, the main portion 39a is designed so that its entire area is consistently exposed by any concave space typically provided despite variations in location over the base 36. Thus, the entire area of the main portion 39a, 0.00115 in$^2$ (as calculated above), remains available for contact with the fluid test sample. However, the variation in location of the concave space 58 results in a different area of each of the secondary portions 39b,c being exposed to the fluid test sample. In this embodiment, the area of the secondary portion 39b exposed to the fluid test sample is increased a certain amount while the area of the secondary portion 39c is decreased a corresponding amount due to the different location of the concave space 58—essentially, the concave space 58 was shifted in the direction of the secondary portion 39b. The exposed width $w_5$ of the secondary portion 39b is 0.013 inches while the exposed width $w_6$ of the secondary portion 39c is 0.007 inches. The height $h_3$ of the secondary portions 39b,c remains 0.005 inches. Accordingly, the area of the secondary portion 39b is 0.000065 $in^2$, while the area of the secondary portion 39c is 0.000035 $in^2$. Thus, the area of the main portion 39a (0.00115 $in^2$) exposed to the fluid test sample remains substantially larger than the areas of the secondary portions 39b, c. Accordingly, the variation in contact area of the secondary portions 39b,c in this embodiment will not significantly affect the meter reading.

Other variations in the location of the concave space (e.g., 48, 58) over the working electrode 39 will also not significantly affect the meter reading. As discussed above, the main portion 39a of the working electrode 39 desirably remains entirely within the concave space, despite variations in its location. Since only a small area of the secondary portions 39b,c is affected by a shift in the location of the concave space, the overall electrical current produced by the entire contacted area of the working electrode 39 will not be significantly affected. As such, the shape of the working electrode 39 is adapted to produce consistently reproducible meter readings with other locations of the concave space (not illustrated). Furthermore, since only a small area of the secondary portions 39b,c would be affected by an adhesive "squeeze-out," as mentioned above, the overall electrical current produced by the entire contacted area of the working electrode 39 would not be significantly affected.

As can be seen in FIGS. 3-4, the main portion 39a of the working electrode 39 fills a large portion of the concave spaces 48 and 58. By filling a large portion along the height (i.e., the height being generally perpendicular to the width $w_1$) of the capillary channel with the main portion 39a of the working electrode 39, the width $w_1$ of the capillary channel may be decreased. In this embodiment, by reducing the width of the capillary channel, the volume of the capillary channel may be reduced to less than about 0.75 μL, preferably less than about 0.6 μL. Thus, another advantage of the present invention is that a smaller capillary channel may be used thereby requiring less blood from a patient for use in filling the concave spaces 48, 58.

Figure 5:
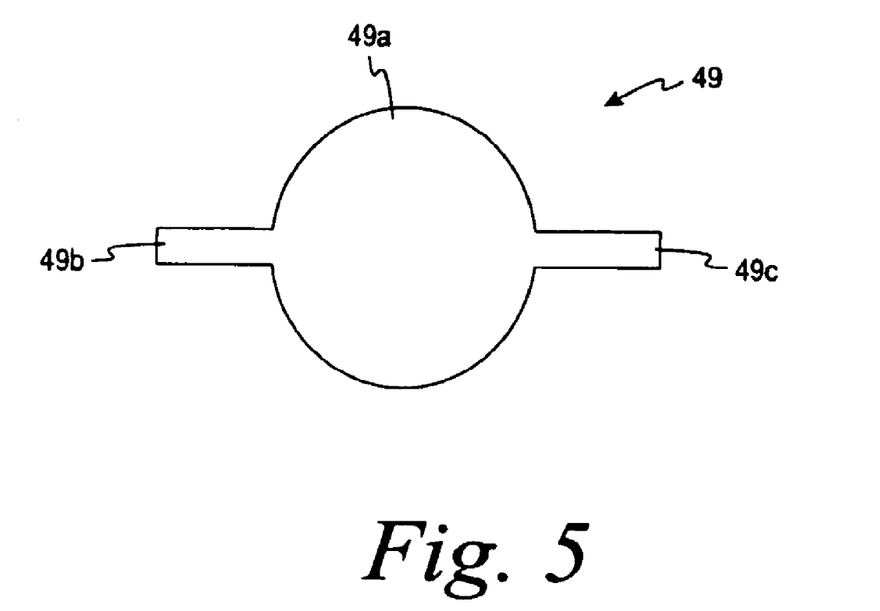
FIGS. 5-8 illustrate an enlarged portion of the working electrode of the electrochemical test sensor according to additional embodiments.

As shown in FIGS. 3-4, the main portion 39a and secondary portions 39b,c of the working electrode 39 are polygonal in shape. However, the working electrode 39 is not limited to the specific shape of FIGS. 3-4. The working electrode 39 will function in accordance with the present invention where the working electrode includes a main portion, exposed to the fluid test sample, that is substantially larger than the secondary portions exposed to the fluid test sample, despite their specific shapes. For example, referring to FIG. 5, a working electrode 49, including a main portion 49a and secondary portions 49b,c, is disclosed according to another embodiment. The shape of the main portion 49a of the working electrode 49 is non-polygonal. It is contemplated that other non-polygonal shapes may be used to form the main portion.

Figure 6:
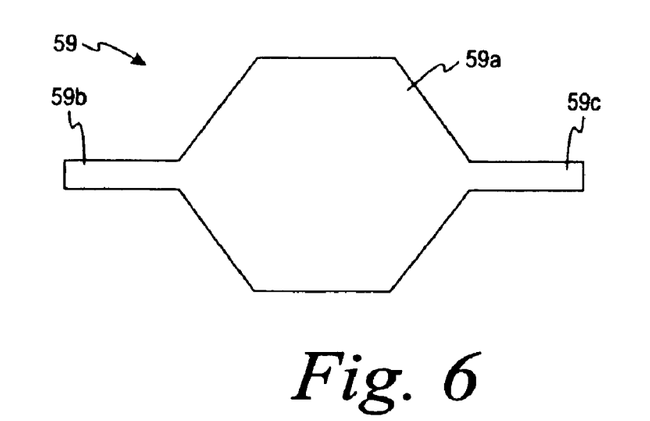
Figure 7:
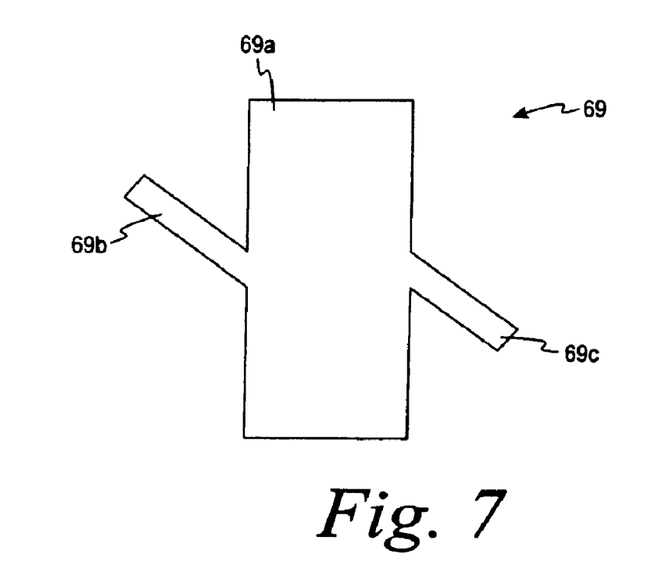
Figure 8:
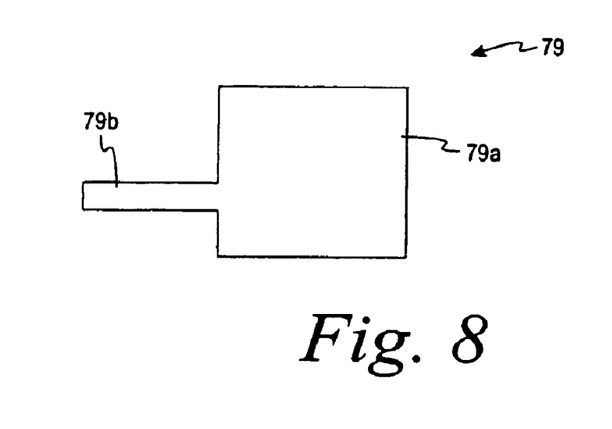

Other shapes of the main portion of the working electrode may also be used. FIG. 6 illustrates a working electrode 59 with a hexagon-shaped main portion 59a and secondary portions 59b,c extending therefrom. The secondary portions may also take other forms than shown. For example, FIG. 7 illustrates a working electrode 69 with a main portion 69a and two secondary portion 69b,c. The secondary portions 69b,c of the working electrode 69 in this embodiment extend diagonally from the main portion 69a of the working electrode. It should also be noted that the secondary portions of the working electrode may also take other, non-rectangular shapes, such as polygonal or non-polygonal shapes. In some embodiments, the working electrode may only include one secondary portion or additional secondary portions. For example, as illustrated in FIG. 8, a working electrode 79 has a main portion 79a with one secondary portion 79b extending therefrom.

While alternative embodiments of the working electrode have been provided above, the working electrode may also take other, non-illustrated, embodiments. Whatever its specific shape, the working electrode should include a voluminous main portion filling a large portion of the capillary channel and at least one smaller secondary portion.

Figure 9:
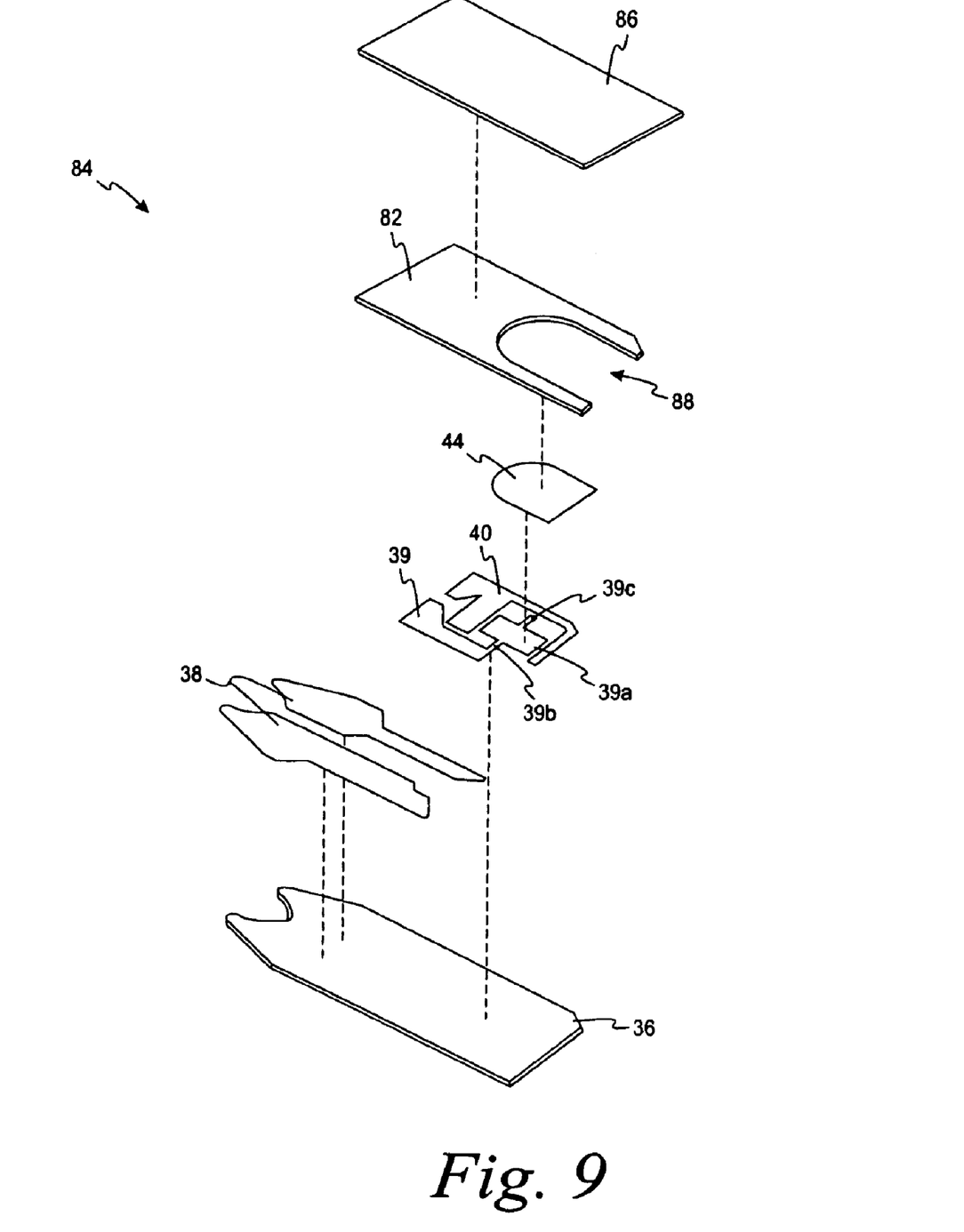
FIG. 9 is an exploded view of an electrochemical test sensor including a spacer according to one embodiment.

The design of the working electrode of the present invention is not limited to use with a three-dimensional embossed lid forming a concave space, such as the lid 46. Other ways of forming a concave space over a working electrode in an electrochemical test sensor may also be used in accordance with the present invention. For example, FIG. 9 depicts an electrochemical test sensor 84 according to another embodiment. The electrochemical test sensor 84 includes the base 36, a meter-contact area 38, the working electrode 39, the counter electrode 40, and the reagent layer 44. The electrochemical test sensor 84 further includes a lid 86 and a spacer 82. The spacer 82 includes a spacer opening 88 formed therein. The spacer opening 88 assists in forming the capillary channel or space when the lid 86 is mated with the spacer 82 and the base 36. The electrochemical test sensor 84 functions in much the same way as electrochemical test sensor 34 with the main difference being the method of forming the spacer opening 88 as compared to the concave space 48. The concave space formed by the spacer opening 88 may vary in location on the base 36 in much the same way the concave space 48 may vary in location as described above. However, the reproducibility of the meter readings is accomplished by the shape of the working electrode 39 in this embodiment in much the same way as described herein in relation to the electrochemical test sensor 34.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

Alternative Embodiment A

An electrochemical test sensor for detecting the concentration of analyte in a fluid test sample, the electrochemical test sensor comprising:

a base that provides a flow path for the fluid test sample having on its surface a counter electrode and a working electrode in electrical communication with a detector of electrical current;

a reagent layer directly located on the surface of the working electrode, the reagent layer including an enzyme that is adapted to react with the analyte; and a lid adapted to mate with the base and to assist in forming a capillary space with an opening for the introduction of fluid test sample thereto, the capillary space being formed with a three-dimensional portion of the lid.

Alternative Embodiment B

The test sensor of Alternative Embodiment A wherein the reagent layer is further located on the surface of the counter electrode.

Alternative Embodiment C

The test sensor of Alternative Embodiment A wherein the area of the working electrode adapted to interact with the analyte of the fluid test sample includes a main portion and at least one secondary portion extending therefrom.

Alternative Embodiment D

The test sensor of Alternative Embodiment C wherein the main portion of the working electrode has a first width in a first direction and the at least one secondary portion has a second width in the first direction, the first width being at least 2 times greater than the second width.

Alternative Embodiment E

The test sensor of Alternative Embodiment D wherein the main portion of the working electrode has a first height in a second direction and the at least one secondary portion has a second height in the second direction, the second direction being generally perpendicular to the first direction, the first height being from about 5 to about 15 times greater than the second height.

Alternative Embodiment F

The test sensor of Alternative Embodiment C wherein the at least one secondary portion of the working electrode is generally polygonal.

Alternative Embodiment G

The test sensor of Alternative Embodiment F wherein the main portion of the working electrode is generally polygonal.

Alternative Embodiment H

The test sensor of Alternative Embodiment F wherein the main portion of the working electrode is generally non-polygonal.

Alternative Embodiment I

The test sensor of Alternative Embodiment A wherein the capillary space is less than about 0.75 μL.

Alternative Embodiment J

The test sensor of Alternative Embodiment A wherein the capillary space is less than about 0.6 μL.

Alternative Embodiment K

An electrochemical test sensor for detecting the concentration of analyte in a fluid test sample, the electrochemical test sensor comprising:

a base that provides a flow path for the fluid test sample having on its surface a counter electrode and a working electrode in electrical communication with a detector of electrical current, the working electrode includes a main portion and at least two secondary portions extending therefrom;

a reagent layer directly located on the surface of the working electrode, the reagent layer including an enzyme that is adapted to react with the analyte; and a lid adapted to mate with the base and to assist in forming a capillary space with an opening for the introduction of fluid test sample thereto.

Alternative Embodiment L

The test sensor of Alternative Embodiment K wherein one of the secondary portions of the working electrode is in electrical communication with the detector.

Alternative Embodiment M

The test sensor of Alternative Embodiment K wherein the main portion of the working electrode is disposed between the at least two secondary portions of the working electrode, the at least two secondary portions of the working electrode being generally opposite from each other.

Alternative Embodiment N

The test sensor of Alternative Embodiment L wherein the area of the main portion of the working electrode is substantially larger than the area of the secondary portions of the working electrode.

Alternative Embodiment O

An electrochemical test sensor for detecting the concentration of analyte in a fluid test sample, the electrochemical test sensor comprising:

a base that provides a flow path for the fluid test sample having on its surface a counter electrode and a working electrode in electrical communication with a detector of electrical current;

a reagent layer directly located on the surface of the working electrode, the reagent layer including an enzyme that is adapted to react with the analyte, the working electrode including a main portion having a first width in a first direction and further including at least one secondary portion extending from the main portion having a second width in the first direction, the first width being at least about 2 times greater than the second width; and a lid adapted to mate with the base and to assist in forming a capillary space with an opening for the introduction of fluid test sample thereto.

Alternative Embodiment P

The test sensor of Alternative Embodiment O further including a spacer that is adapted to assist in forming the capillary opening, the spacer being located between the base and the lid.

Alternative Embodiment Q

The test sensor of Alternative Embodiment O wherein the main portion of the working electrode has a first height in a second direction and the at least one secondary portion has a second height in the second direction, the second direction being generally perpendicular to the first direction, the first height being from about 5 to about 15 times greater than the second height.

Alternative Embodiment R

The test sensor of Alternative Embodiment O wherein the at least one secondary portion of the working electrode is generally polygonal.

Alternative Embodiment S

The test sensor of Alternative Embodiment R wherein the main portion of the working electrode is generally polygonal.

Alternative Embodiment T

The test sensor of Alternative Embodiment R wherein the main portion of the working electrode is generally non-polygonal.

Alternative Embodiment U

The test sensor of Alternative Embodiment S wherein the capillary space is less than about 0.75 µL.

Alternative Embodiment V

The test sensor of Alternative Embodiment S wherein the capillary space is less than about 0.6 µL.

Alternative Process W

A method for determining the concentration of an analyte in a fluid test sample with a test sensor, the method comprising the acts of:
providing a base that provides a flow path for the fluid test sample having on its surface a counter electrode and a working electrode in electrical communication with a detector of electrical current, the working electrode includes a main portion and at least two secondary portions extending therefrom, a reagent layer being directly located on the surface of the working electrode, the reagent layer including an enzyme that is adapted to react with the analyte, a lid being adapted to mate with the base and to assist in forming a capillary space with an opening for the introduction of fluid test sample thereto;
contacting the reagent layer with the fluid sample via the capillary space;
generating an electrical signal in the test sensor in response to the presence of the analyte; and
determining the concentration of the analyte from the electrical signal.

Alternative Process X

A method for determining the concentration of an analyte in a fluid sample with a test sensor, the method comprising the acts of:
providing an electrochemical test sensor comprising a base that provides a flow path for the fluid test sample having on its surface a counter electrode and a working electrode in electrical communication with a detector of electrical current, a reagent layer being directly located on the surface of the working electrode, the reagent layer including an enzyme that is adapted to react with the analyte, and a lid being adapted to mate with the base and to assist in forming a capillary space with an opening for the introduction of fluid test sample thereto, the capillary space being formed with a three-dimensional portion of the lid;
contacting the reagent layer with the fluid sample via the capillary space;
generating an electrical signal in the test sensor in response to the presence of the analyte; and
determining the concentration of the analyte from the electrical signal.

Alternative Process Y

The method of Alternative Process X wherein the working electrode includes a main portion and at least two secondary portions adapted to interact with the liquid sample.

Alternative Process Z

The method of Alternative Process Y wherein the area of the main portion of the working electrode is at least 10 times the area of the at least two secondary portions of the working electrode adapted to interact with the fluid sample.

Alternative Process AA

The method of Alternative Process X wherein the analyte is glucose.

Alternative Process BB

The method of Alternative Process X wherein the capillary space is less than about 0.75 µL.

What is claimed is:

1. An electrochemical test sensor for detecting the concentration of an analyte in a fluid test sample, the electrochemical test sensor comprising:
a base that provides a flow path for the fluid test sample having on its surface a counter electrode and a working electrode in electrical communication with a detector of electrical current, the working electrode including a main portion and at least one secondary portion extending therefrom;
a reagent layer directly located on the surface of at least a part of the main portion of the working electrode and at least a part of the at least one secondary portion of the working electrode, the reagent layer including an enzyme that reacts with the analyte; and
a lid that mates with the base to form a capillary space with an opening for the introduction of fluid test sample thereto, the capillary space being defined by the base and the lid such that the fluid test sample contacts the main portion after being introduced to the capillary space; and
a spacer located between the base and the lid, the spacer including a spacer opening that assists in forming the capillary space, the capillary space being defined by the base, the spacer, and the lid.

2. The test sensor of claim 1, wherein the reagent layer is further located on the surface of the counter electrode.

3. The test sensor of claim 1, wherein the main portion of the working electrode has a first width in a first direction and the at least one secondary portion has a second width in the first direction, the first width being at least 2 times greater than the second width.

4. The test sensor of claim 3, wherein the main portion of the working electrode has a first height in a second direction and the at least one secondary portion has a second height in the second direction, the second direction being generally perpendicular to the first direction, the first height being from about 5 to about 15 times greater than the second height.

5. The test sensor of claim 1, wherein the at least one secondary portion of the working electrode is generally polygonal.

6. The test sensor of claim 5, wherein the main portion of the working electrode is generally polygonal.

7. The test sensor of claim 5, wherein the main portion of the working electrode is generally non-polygonal.

8. The test sensor of claim 1, wherein the capillary space is less than about 0.75 μL.

9. The test sensor of claim 1, wherein the capillary space is less than about 0.6 μL.

10. The test sensor of claim 1, wherein the main portion of the working electrode is disposed between at least two secondary portions of the working electrode, the at least two secondary portions of the working electrode being generally opposite from each other.

11. The test sensor of claim 1, wherein the area of the main portion of the working electrode is larger than the area of the at least one secondary portion of the working electrode.

12. The test sensor of claim 1, wherein the lid includes a three-dimensional portion, the capillary space being defined by the base and the three-dimensional portion of the lid.

13. A method for determining the concentration of an analyte in a fluid sample with a test sensor, the method comprising the acts of:

providing an electrochemical test sensor comprising a base that provides a flow path for the fluid test sample having on its surface a counter electrode and a working electrode in electrical communication with a detector of electrical current, the working electrode including a main portion and at least one secondary portion extending therefrom, a reagent layer being directly located on the surface of at least a part of the main portion of the working electrode and at least a part of the at least one secondary portion of the working electrode, the reagent layer including an enzyme that reacts with the analyte, and a lid that mates with the base to form a capillary space with an opening for the introduction of fluid test sample thereto, the capillary space being defined by the base and the lid such that the fluid test sample contacts the main portion after being introduced to the capillary space, the electrochemical test sensor further comprising a spacer located between the base and the lid, the spacer including a spacer opening that assists in forming the capillary space, the capillary space being defined by the base, the spacer, and the lid;

contacting the reagent layer with the fluid sample via the capillary space;

generating an electrical signal in the test sensor in response to the presence of the analyte; and determining the concentration of the analyte from the electrical signal.

14. The method of claim 13, wherein the area of the main portion of the working electrode is at least 10 times the area of the at least two secondary portions of the working electrode adapted to interact with the fluid sample.

15. The method of claim 13, wherein the analyte is glucose.

16. The method of claim 13, wherein the capillary space is less than about 0.75 μL.

17. The method of claim 13, wherein the main portion of the working electrode has a first width in a first direction and the at least one secondary portion has a second width in the first direction, the first width being at least 2 times greater than the second width.

18. An electrochemical test sensor for detecting the concentration of an analyte in a fluid test sample, the electrochemical test sensor comprising:

a base that provides a flow path for the fluid test sample having on its surface a counter electrode and a working electrode in electrical communication with a detector of electrical current, the working electrode including a main portion and at least one secondary portion extending therefrom;

a reagent layer directly located on the surface of at least a part of the main portion of the working electrode and at least a part of the at least one secondary portion of the working electrode, the reagent layer including an enzyme that reacts with the analyte;

a lid that mates with the base to form a capillary space with an opening for the introduction of fluid test sample thereto; and a spacer located between the base and the lid, the capillary space being defined by the base, the spacer, and the lid such that the fluid test sample contacts the main portion after being introduced to the capillary space, the working electrode being exposed to the fluid test sample without a dielectric layer located on the working electrode.

* * * * *